United States Patent
Shimokawa et al.

(10) Patent No.: US 11,369,601 B2
(45) Date of Patent: Jun. 28, 2022

(54) PROPHYLACTIC OR THERAPEUTIC AGENT FOR PULMONARY HYPERTENSION COMPRISING MEBENDAZOLE AND/OR ITRACONAZOLE OR SALT THEREOF

(71) Applicant: TOHOKU UNIVERSITY, Miyagi (JP)

(72) Inventors: Hiroaki Shimokawa, Miyagi (JP); Kimio Satoh, Miyagi (JP); Junichi Omura, Miyagi (JP); Nobuhiro Kikuchi, Miyagi (JP); Ryo Kurosawa, Miyagi (JP)

(73) Assignee: TOHOKU UNIVERSITY, Miyagi (JP)

(*) Notice: Subject to any disclaimer, the term of this patent is extended or adjusted under 35 U.S.C. 154(b) by 25 days.

(21) Appl. No.: 16/769,008

(22) PCT Filed: Nov. 30, 2018

(86) PCT No.: PCT/JP2018/044306
§ 371 (c)(1),
(2) Date: Jun. 2, 2020

(87) PCT Pub. No.: WO2019/111829
PCT Pub. Date: Jun. 13, 2019

(65) Prior Publication Data
US 2021/0220350 A1    Jul. 22, 2021

(30) Foreign Application Priority Data
Dec. 5, 2017    (JP) .............................. JP2017-233034

(51) Int. Cl.
*A61K 31/496* (2006.01)
*A61K 9/00* (2006.01)
*A61K 31/4184* (2006.01)

(52) U.S. Cl.
CPC .......... *A61K 31/496* (2013.01); *A61K 9/0053* (2013.01); *A61K 31/4184* (2013.01)

(58) Field of Classification Search
CPC ....... A61K 31/496; A61K 9/0053; A61P 9/12; A61P 11/00
See application file for complete search history.

(56) References Cited

FOREIGN PATENT DOCUMENTS

| WO | 2006/004795 | 1/2006 |
| WO | 2018/115319 | 6/2018 |

OTHER PUBLICATIONS

Sakao et al., Respiratory Research, 2009, 10:95 (Year: 2009).*
Mukhopadhyay et al., Clin Cancer Res Sep. 2002;8(9):2963-9 (Year: 2002).*
Aftab et al., Cancer Res 2011;71(21):6764-72 (Year: 2011).*
(Continued)

*Primary Examiner* — San Ming R Hui
(74) *Attorney, Agent, or Firm* — Wenderoth, Lind & Ponack, L.L.P.

(57) ABSTRACT

An object to be achieved by the present invention is to provide a novel preventive or therapeutic agent for pulmonary hypertension containing as an active ingredient a compound that has not been known for a therapeutic effect on pulmonary hypertension heretofore. The present invention provides a preventive or therapeutic agent for pulmonary hypertension, including at least one kind selected from the group consisting of mebendazole and itraconazole or a salt thereof.

3 Claims, 2 Drawing Sheets

(56) References Cited

OTHER PUBLICATIONS

International Search Report dated Jan. 15, 2019 in International (PCT) Application No. PCT/JP2018/044306.
Chong et al., "Inhibition of Angiogenesis by the Antifungal Drug Itraconazole", ACS Chem. Biol., 2007, vol. 2, No. 4, pp. 263-270.
Nacev et al., "The Antifungal Drug Itraconazole Inhibits Vascular Endothelial Growth Factor Receptor 2 (VEGFR2) Glycosylation, Trafficking, and Signaling in Endothelial Cells", J. Biol. Chem., 2011, vol. 286, No. 51, pp. 44045-44056.
Head et al., "Antifungal drug itraconazole targets VDAC1 to modulate the AMPK/mTOR signaling axis in endothelial cells", Proc. Natl. Acad. Sci. U.S.A., 2015, vol. 112, No. 52, pp. E7276-E7285.
Dakshanamurthy et al., "Predicting New Indications for Approved Drugs Using a Proteochemometric Method", J. Med. Chem., 2012, vol. 55, pp. 6832-6848.
Wang et al., "Mebendazole Reduces Vascular Smooth Muscle Cell Proliferation and Neointimal Formation Following Vascular Injury in Mice", PLoS ONE, 2014, vol. 9, No. 2, e90146, pp. 1-7.
Goncharova, "mTOR and vascular remodeling in lung diseases: current challenges and therapeutic prospects", FASEB J., 2013, vol. 27, No. 5, pp. 1796-1807.
Yamaji-Kegan, K. et al., "Hypoxia-induced mitogenic factor has proangiogenic and proinflammatory effects in the lung via VEGF and VEGF receptor-2", Am J. Physiol. Lung Cell. Mol. Physiol., 2006, vol. 291, pp. L1159-L1168.
Purcell, I. F. et al., "Use of nebulised liposomal amphotericin B in the treatment of *Aspergillus fumigatus* empyema", Thorax, 1995, vol. 50, pp. 1321-1323.
Mehta et al., "Reversible Pulmonary Hypertension Due to Fibrosing Mediastinitis", Chest, 2016, vol. 150, No. 4, supply, p. 181A.
Rabinovitch et al., "Molecular pathogenesis of pulmonary arterial hypertension", The Journal of Clinical Investigation, 2012, vol. 122, No. 12, pp. 4306-4313.
Satoh et al., "Basigin Mediates Pulmonary Hypertension by Promoting Inflammation and Vascular Smooth Muscle Cell Proliferation", Circulation Research, 2014, vol. 115, pp. 738-750.
Satoh et al., "Statin ameliorates hypoxia-induced pulmonary hypertension associated with down-regulated stromal cell-derived factor-1", Cardiovascular Research, 2009, vol. 81, pp. 226-234.
Satoh et al., "Important Role of Endogenous Erythropoietin System in Recruitment of Endothelial Progenitor Cells in Hypoxia-Induced Pulmonary Hypertension in Mice Circulation", Circulation, 2006, vol. 113, pp. 1442-1450.
Shimizu et al. "Crucial Role of ROCK2 in Vascular Smooth Muscle Cells for Hypoxia-Induced Pulmonary Hypertension in Mice", Arterioscler. Thromb. Vasc. Biol. 2013, vol. 33, pp. 2780-2791.
Extended European Search Report dated Aug. 2, 2021 in corresponding European Patent Application No. 18885573.8.
Peter Carmeliet, "Angiogenesis in Health and Disease", Nature Medicine, Jun. 2003, vol. 9, No. 6, pp. 653-660.

\* cited by examiner

PROPHYLACTIC OR THERAPEUTIC AGENT FOR PULMONARY HYPERTENSION COMPRISING MEBENDAZOLE AND/OR ITRACONAZOLE OR SALT THEREOF

CROSS-REFERENCE TO RELATED APPLICATION

This application claims priority from Japanese Patent Application No. 2017-233034, filed on Dec. 5, 2017, the entire disclosure of which is incorporated herein by reference. The present invention relates to a preventive or therapeutic agent for pulmonary hypertension.

BACKGROUND ART

Pulmonary hypertension is a disease involving increased blood pressure in pulmonary arteries, which carry blood from heart to lungs, leading to impaired cardiac and pulmonary functions, and is a disease quite different from a symptom generally called "hypertension". In addition, pulmonary hypertension is a severe disease with high lethality, and hence there is an urgent need to develop a therapeutic method therefor.

Conventional treatments for pulmonary hypertension include vasodilation treatment using a catheter, and treatment such as surgical removal of thrombus, but less invasive therapeutic methods are desired. In addition, a vasodilator or the like is known as medication (e.g., Non-patent Literature 1), but there are still a large number of patients that cannot be saved by such therapeutic method. Thus, there is a strong demand for further development of a therapeutic agent for pulmonary hypertension.

CITATION LIST

Non-Patent Literature

NPL 1: J Clin Invest. 2012; 122(12): 4306-4313
NPL 2: Satoh et al., Circ. Res. 2014, 115, 738-750.
NPL 3: Satoh et al., Cardiovasc. Res. 2009, 81, 226-234.
NPL 4: Satoh et al., Circulation, 2006, 113, 1442-1450.
NPL 5: Shimizu et al., Arterioscler. Thromb. Vasc. Biol. 2013, 33, 2780-2791.

SUMMARY OF INVENTION

Technical Problem

The present invention provides a novel preventive or therapeutic agent for pulmonary hypertension containing as an active ingredient a compound that has not been known for a therapeutic effect on pulmonary hypertension heretofore.

Solution to Problem

Under such circumstances, the inventors of the present invention have investigated thousands of kinds of compounds. As a result, the inventors have found that mebendazole and/or itraconazole suppresses excessive proliferation of pulmonary artery smooth muscle cells, which is supposed to be one of the causes for pulmonary hypertension, and has preventive and therapeutic effects on pulmonary hypertension. The present invention is based on such novel findings.

Thus, the present invention provides the following items:

Item 1. A preventive or therapeutic agent for pulmonary hypertension, including at least one kind selected from the group consisting of mebendazole and itraconazole or a salt thereof.

Item 2. The preventive or therapeutic agent for pulmonary hypertension according to Item 1, wherein the preventive or therapeutic agent for pulmonary hypertension includes mebendazole or a salt thereof.

Item 3. The preventive or therapeutic agent for pulmonary hypertension according to Item 1 or 2, wherein the preventive or therapeutic agent for pulmonary hypertension is an orally administered agent.

Item 4-1. A method of preventing or treating pulmonary hypertension, including administering an effective dose of at least one kind selected from the group consisting of mebendazole and itraconazole or a salt thereof as a preventive or therapeutic agent for pulmonary hypertension to a subject.

Item 4-2. The method according to Item 4-1, wherein the preventive or therapeutic agent for pulmonary hypertension includes mebendazole or a salt thereof.

Item 4-3. The method according to Item 4-1 or 4-2, wherein the preventive or therapeutic agent for pulmonary hypertension is an orally administered agent.

Item 5-1. At least one kind selected from the group consisting of mebendazole and itraconazole or a salt thereof, for use in prevention or treatment of pulmonary hypertension.

Item 5-2. The compound or the salt thereof according to Item 5-1, wherein the compound or the salt thereof is mebendazole or a salt thereof.

Item 5-3. The compound or the salt thereof according to Item 5-1 or 5-2, wherein the prevention or treatment of pulmonary hypertension is performed by orally administering the at least one kind selected from the group consisting of mebendazole and itraconazole or the salt thereof.

Item 6-1. A use of at least one kind selected from the group consisting of mebendazole and itraconazole or a salt thereof, for manufacture of a preventive or therapeutic agent for pulmonary hypertension.

Item 6-2. The use according to Item 6-1, wherein the at least one kind selected from the group consisting of mebendazole and itraconazole or the salt thereof is mebendazole or a salt thereof.

Item 6-3. The use according to Item 6-1 or 6-2, wherein the preventive or therapeutic agent for pulmonary hypertension is an orally administered agent.

Advantageous Effects of Invention

According to the present invention, the novel preventive or therapeutic agent for pulmonary hypertension can be provided by using mebendazole or a salt thereof and/or itraconazole or a salt thereof, each of which is a compound that has not been known for a therapeutic effect on pulmonary hypertension heretofore, as an active ingredient.

DESCRIPTION OF EMBODIMENTS

Figure 1:
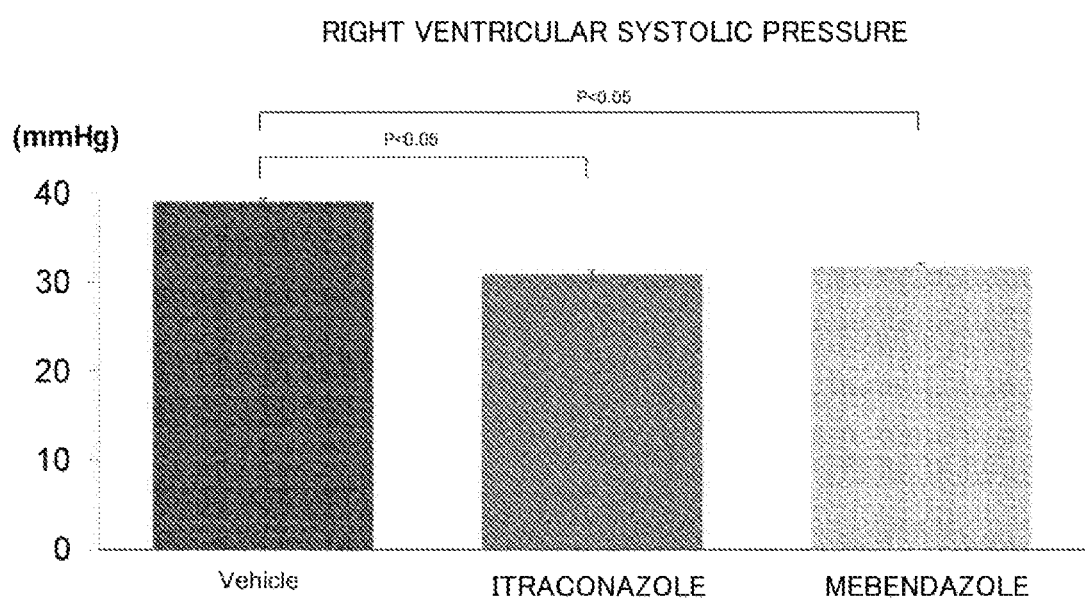
FIG. 1 shows the measurement results of right ventricular systolic pressure in Example 1.

Preventive or Therapeutic Agent for Pulmonary Hypertension

The present invention provides a preventive or therapeutic agent for pulmonary hypertension containing at least one kind selected from the group consisting of mebendazole and itraconazole or a salt thereof. Herein, at least one kind of compound selected from the group consisting of mebendazole and itraconazole is sometimes collectively abbreviated simply as "compound A". Accordingly, the present invention provides a preventive or therapeutic agent for pulmonary hypertension containing a compound A or a salt thereof.

Mebendazole [CAS No. 31431-39-7, methyl (5-benzoyl-1H-benzo[d]imidazol-2-yl)carbamate] serving as an active ingredient of the present invention is a known substance having the following structure:

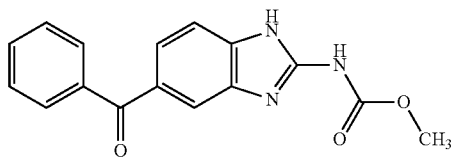 [SMILES: COC(=O)Nc1nc2cc(C(=O)c3ccccc3)ccc2[nH]1]

The salt of mebendazole serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine.

Itraconazole serving as an active ingredient of the present invention [CAS No. 84625-61-6, 4-(4-(4-(4-(((2R,4S)-2-((1H-1,2,4-triazol-1-yl)methyl)-2-(2,4-dichlorophenyl)-1,3-dioxolan-4-yl)methoxy)phenyl)piperazin-1-yl)phenyl)-2-(sec-butyl)-2,4-dihydro-3H-1,2,4-triazol-3-one] is a known substance having the following structure:

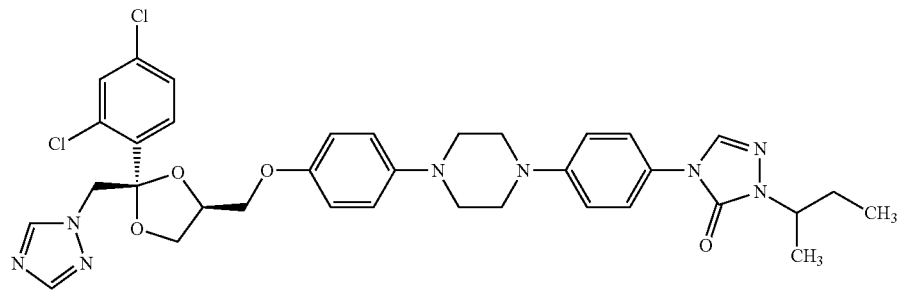 [SMILES: CCC(C)n1ncn(-c2ccc(N3CCN(c4ccc(OC[C@H]5CO[C@](Cn6cncn6)(c6ccc(Cl)cc6Cl)O5)cc4)CC3)cc2)c1=O]

The salt of itraconazole serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine.

In the present invention, of the compounds A or the salts thereof, mebendazole or a salt thereof is preferred.

The compound A and the salt thereof serving as the active ingredient of the present invention may be present in the form of a hydrate or a solvate, and hence the compound serving as the active ingredient of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and DMSO. Those solvents may be used alone or as a mixed solvent thereof.

In the present invention, the compound A or the salt thereof serving as the active ingredient of the present invention may be used alone as a preventive or therapeutic agent for pulmonary hypertension, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride. Those tonicity agents may be used alone or in combination thereof.

Examples of the chelating agent include: edentates, such as disodium edetate, calcium disodium edetate, trisodium edetate, tetrasodium edetate, and calcium edetate; ethylenediaminetetraacetate; nitrilotriacetic acid or salts thereof; sodium hexametaphosphate; and citric acid. Those chelating agents may be used alone or in combination thereof.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol. Those pH regulators may be used alone or in combination thereof.

Examples of the preservative include: sorbic acid; potassium sorbate; parahydroxybenzoates, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; and chlorhexidine. Those preservatives may be used alone or in combination thereof.

Examples of the antioxidant include sodium hydrogen sulfite, dried sodium sulfite, sodium pyrosulfite, and concentrated mixed tocopherols. Those antioxidants may be used alone or in combination thereof.

Examples of the solubilizing agent include sodium benzoate, glycerin, D-sorbitol, glucose, propylene glycol, hydroxypropyl methylcellulose, polyvinylpyrrolidone, macrogol, and D-mannitol. Those solubilizing agents may be used alone or in combination thereof.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol. Those thickening agents may be used alone or in combination thereof.

In addition, the pharmaceutical composition may further contain, in addition to the compound A or the salt thereof, a compound known to have a preventive or therapeutic action on pulmonary hypertension. Examples of the compound known to have a preventive or therapeutic action on pulmonary hypertension include a prostacyclin preparation (e.g., epoprostenol), a PDE5 inhibitor (e.g., tadalafil), and an endothelin receptor antagonist (e.g., bosentan). Those compounds may be used alone or in combination thereof.

In the embodiment of the pharmaceutical composition, the content of the compound A or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of the compound A.

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet, a pill, a capsule, a powder, a granule, and a syrup) and external preparations (e.g., an inhalant, an ointment, a cream, and a patch) are preferred.

In the present invention, the dose of the compound A or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less in terms of the dose of the compound A. In addition, according to the present invention, the compound A exhibits an effect even at a low dose, and hence the dose may be, for example, such an amount that a daily dose for adults is about 100 mg or less, about 10 mg or less, about 8 mg or less, or about 5 mg or less in terms of the dose of the compound A. The lower limit of the dose of the compound A or the salt thereof is also not particularly limited, and may be appropriately set within, for example, such a range that a daily dose for adults is generally 0.1 mg or more, preferably 0.5 mg or more in terms of the dose of the compound A. When administered once daily, the compound A or the salt thereof only needs to be contained in the above-mentioned amount in a single dose. When administered three times daily, the compound A or the salt thereof only needs to be contained in an amount corresponding to one-third of the above-mentioned amount in a single dose.

The preventive or therapeutic agent for pulmonary hypertension of the present invention is administered to patients, such as mammals. Examples of the mammals include humans, monkeys, mice, rats, rabbits, cats, dogs, pigs, cattle, horses, and sheep.

The preventive or therapeutic agent for pulmonary hypertension of the present invention prevents or treats and ameliorates pulmonary hypertension by at least suppressing excessive proliferation of pulmonary artery smooth muscle cells. Accordingly, the present invention also provides a suppressor for excessive proliferation of pulmonary artery smooth muscle cells containing a compound A or a salt thereof.

Mebendazole serving as the active ingredient of the present invention is in wide use as an antiparasitic agent throughout the world including Japan, but is not known at all for an effect on pulmonary hypertension. In addition, itraconazole serving as the active ingredient of the present invention is in use as an antifungal medication, but is not known at all for an effect on pulmonary hypertension. Thus, the suppressive effect of the compound A or the salt thereof on excessive proliferation of pulmonary artery smooth muscle cells and the preventive or therapeutic effect of the compound A or the salt thereof on pulmonary hypertension in the present invention are unpredictable from the related art. The active ingredient, dosage form, dose, and the like of the suppressor for excessive proliferation of pulmonary artery smooth muscle cells are the same as those of the preventive or therapeutic agent for pulmonary hypertension.

The present invention is more specifically described below by way of Examples. However, the present invention is not limited thereto.

EXAMPLES

Example 1

Hypoxia-induced pulmonary hypertension mice serving as a model generally used in an animal experiment for pulmonary hypertension were intravenously administered itraconazole or mebendazole. Specifically, first, 8-week-old male wild-type mice (C57/BL6 mice, n=10 per group) were housed in a transparent acrylic box with an oxygen concentration controlled to 10% using a hypoxia generator (Teijin Limited, Japan) under a 12 h light and dark cycle. The mice were stimulated by hypoxia for 3 weeks, and in this period, were intravenously injected with itraconazole (the following solution was used as itraconazole: 100 mg of itraconazole was dissolved in 6.7 ml of dimethyl sulfoxide, and the solution of itraconazole in dimethyl sulfoxide was mixed with ultrapure water (mQ or ultrapure water) to prepare a 100 ml solution) once daily at a dose of 20 mg/kg/day. As a Vihicle group, the following test was performed: the mice were stimulated by hypoxia in the same manner as described above except that the mice were intravenously injected with a 1:15 (V/V) mixed solution of dimethyl sulfoxide and ultrapure water in place of itraconazole as a diet. In addition, a mebendazole administration test for hypoxia-induced pulmonary hypertension mice was performed in the same manner as described above except that the mice were intravenously injected with mebendazole in place of itraconazole (the following solution was used as mebendazole: 100 mg of mebendazole was dissolved in 6.7 ml of dimethyl sulfoxide, and the solution of mebendazole in dimethyl sulfoxide was mixed with ultrapure water (mQ or ultrapure water) to prepare a 100 ml solution) at a dose of 25 mg/kg/day.

Assessment Method: Assessment of Pulmonary Hypertension

After the hypoxic stimulation for 3 weeks, a 1.2-Fr catheter (SciSense Inc., Ontario, Canada) was inserted in the jugular vein of the mice under isoflurane anesthesia and advanced into the right ventricle to measure a right ventricular systolic pressure. The results are shown in FIG. 1. The average body weights of the Vehicle group, the itraconazole administration group, and the mebendazole administration group before the test were 16.3±0.2 g, 16.8±0.3 g, and 16.8.±0.3 g, respectively. In addition, the average body weights of the Vehicle group, the itraconazole administration group, and the mebendazole administration group after the test were 18.±0.2 g, 17.2±0.2 g, and 17.5±0.2 g, respectively.

Results and Discussion

Significant reductions in right ventricular systolic pressure and right ventricular hypertrophy were found in the group administered itraconazole or mebendazole by intravenous injection and mixed feed (FIG. 1).

Example 2

In order to further assess the therapeutic effect of mebendazole on pulmonary arterial hypertension (PAH), another pulmonary hypertension animal model was used. A specific procedure is as follows:

Method

Animal Test

In this test, a vehicle treatment group was used as a control. A Sugen/hypoxia-induced hypertension rat model was used to assess pulmonary hypertension (PH) (Non-patent Literature 2). In order to assess the development of pulmonary hypertension, right ventricular systolic pressure (RVSP) and right ventricular hypertrophy (RVH) were measured (Non-patent Literatures 2 to 4).

For right heart catheterization, a 1.4-F (for rats) pressure measurement catheter (Transonic Scisense) was inserted into the right jugular vein and advanced into the right ventricle to measure RVSP (Non-patent Literature 5).

In the Sugen/hypoxia model, rats (Sprague-Dawley, male, 6-week-old) were injected subcutaneously with a VEGF-receptor inhibitor SU5416 (Sigma-Aldrich, St Louis, Mo.) (20 mg per kg body weight) under isoflurane anesthesia and were then exposed to hypoxia (10% $O_2$) for 3 weeks. After the indicated period of treatment below, the rats were anesthetized with isoflurane (1.5%) to perform right heart catheterization. All data were analyzed using the PowerLab data acquisition system (AD Instruments, Bella Vista, Australia) and were averaged over 50 sequential beats (Non-patent Literatures 2 to 5).

Assessment of Right Ventricular Hypertrophy

Hearts were dissected and the right ventricular free wall (RV) was removed from the left ventricle (LV) and septum. The ratio of right ventricular free wall (RV) weight to left ventricle plus septum (LV+Septum) weight [RV/(LV+S)] was measured to assess the extent of RVH (Non-patent Literature 2).

Mebendazole Treatment in Rats with Sugen/Hypoxia-Induced PH

Rats (Sprague-Dawley, male, 6-week-old) were injected subcutaneously with a VEGF-receptor inhibitor SU5416 (Sigma-Aldrich) (20 mg per kg body weight) under isoflurane anesthesia and were then exposed to hypoxia (10% 02) for 3 weeks (hypoxia+SU5416). On day 21, the rats were randomized to be intravenously injected with mebendazole (25 mg per kg body weight) or vehicle (the rats were administered dimethyl sulfoxide in place of mebendazole solution) once daily under normoxia (21% $O_2$) for 2 weeks. The vehicle administration group is expressed as vehicle control. There was no significant difference in body weight between the mebendazole group and the vehicle control group. On day 35, the rats were anesthetized with isoflurane (1.0%) to measure RVSP and RVH. Thus, the development of PH was assessed.

Results

Figure 2:
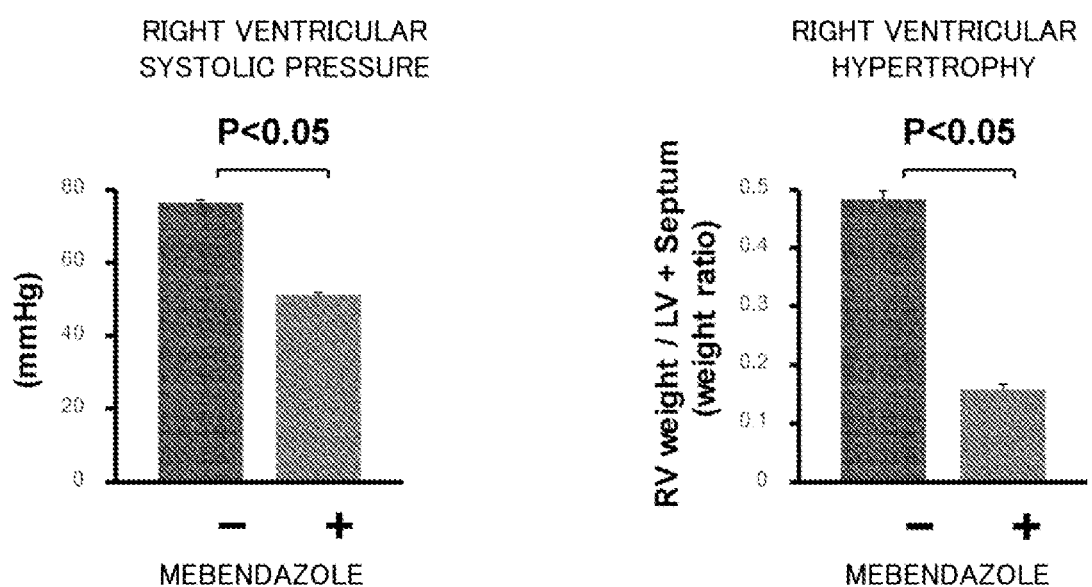
FIG. 2 shows the measurement results of right ventricular systolic pressure (RVSP) and right ventricular hypertrophy (RVH) in Example 2.

The administration of mebendazole for 14 days had no influence on the body weight. However, the RVSP and the RVH were reduced by the mebendazole treatment as compared to the vehicle control (FIG. 2). As described above, mebendazole ameliorated PH in the animal model in vivo. Comparisons of parameters were performed with one-way or two-way ANOVA and Tukey's HSD test for multiple comparisons.

The invention claimed is:

1. A method of treating pulmonary hypertension, comprising administering an effective dose of at least one compound selected from the group consisting of mebendazole and itraconazole or a salt thereof to a subject in need thereof.

2. The method according to claim 1, wherein the mebendazole or a salt thereof is administered to the subject in need thereof.

3. The method according to claim 1, wherein the effective dose of the at least one compound selected from the group consisting of mebendazole and itraconazole or a salt thereof is orally administered to the subject in need thereof.

* * * * *